United States Patent
Swanda et al.

(10) Patent No.: US 8,931,208 B2
(45) Date of Patent: Jan. 13, 2015

(54) AUTOMATED SYSTEM AND METHODS FOR SEPARATING AND SINGULATING PLANT EMBRYOS

(71) Applicant: Weyerhaeuser NR Company, Federal Way, WA (US)

(72) Inventors: Anthony P. Swanda, Snoqualmie, WA (US); Robert A. Starr, Auburn, WA (US); Amy M. Jamruszka-Lewis, Sumner, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 239 days.

(21) Appl. No.: 13/718,860

(22) Filed: Dec. 18, 2012

(65) Prior Publication Data
US 2013/0167438 A1    Jul. 4, 2013

Related U.S. Application Data

(60) Provisional application No. 61/581,478, filed on Dec. 29, 2011.

(51) Int. Cl.
*A01C 1/06* (2006.01)
*A01H 4/00* (2006.01)

(52) U.S. Cl.
CPC . *A01C 1/06* (2013.01); *A01H 4/005* (2013.01)
USPC ........................................................... 47/57.6

(58) Field of Classification Search
USPC ........ 47/1.01 P, 58.1 SE, 57.6; 435/410, 420, 435/430, 430.1
See application file for complete search history.

(56) References Cited

U.S. PATENT DOCUMENTS

| 4,676,142 A | 6/1987 | McCormick et al. |
| 2008/0015790 A1 | 1/2008 | Timmis et al. |
| 2009/0087908 A1 | 4/2009 | Jamruska |
| 2011/0076715 A1 | 3/2011 | Swanda |

FOREIGN PATENT DOCUMENTS

| WO | 0113702 A2 | 3/2001 |
| WO | 2011042888 A2 | 4/2011 |

*Primary Examiner* — Monica Williams
(74) *Attorney, Agent, or Firm* — Christensen O'Connor Johnson & Kindness PLLC

(57) ABSTRACT

The present invention is directed to an automated system and methods for separating and singulating plant embryos.

17 Claims, 14 Drawing Sheets

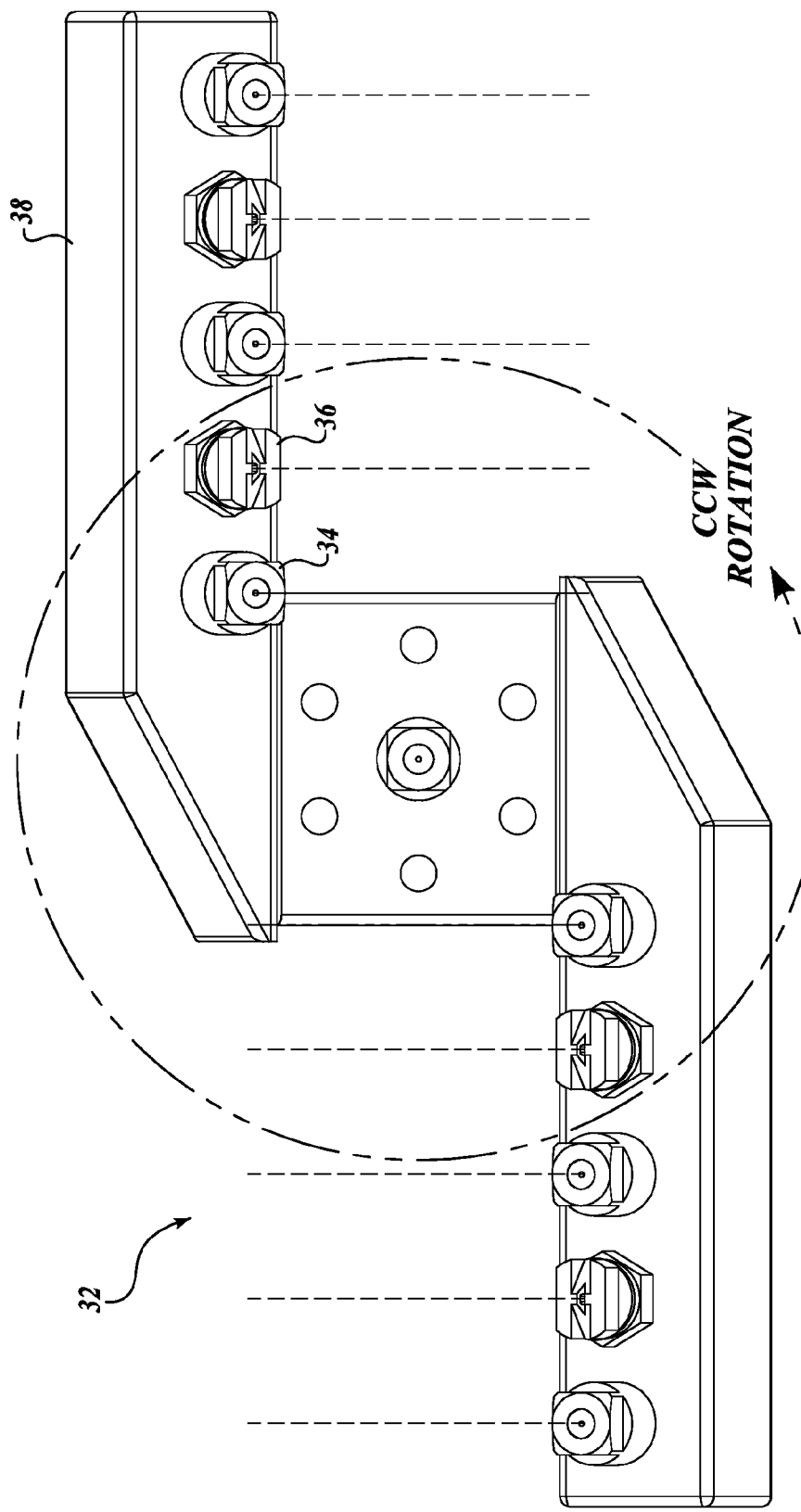

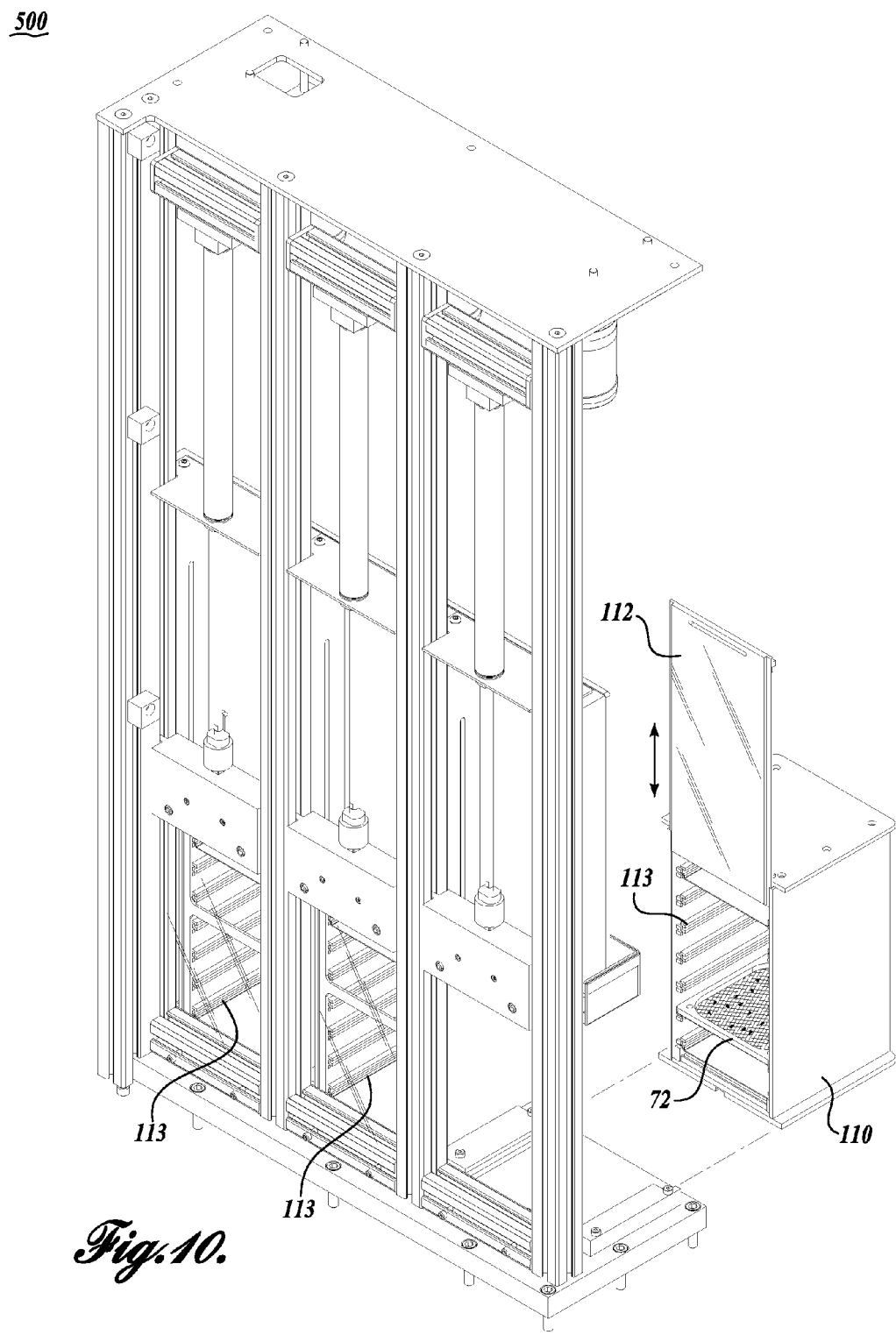

AUTOMATED SYSTEM AND METHODS FOR SEPARATING AND SINGULATING PLANT EMBRYOS

CROSS-REFERENCE TO RELATED APPLICATION

This application is entitled to and claims the benefit of priority under 35 U.S.C. §119 from U.S. Provisional Patent Application Ser. No. 61/581,478 filed Dec. 29, 2011, and titled "AUTOMATED SYSTEM AND METHODS FOR SEPARATING AND SINGULATING PLANT EMBRYOS," the contents of which are incorporated herein by reference

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as embryogenic suspensor masses, that are capable of developing into somatic embryos. The embryogenic tissue is then further cultured in a multiplication medium that promotes multiplication and mass production of the embryogenic tissue. The embryogenic tissue is then cultured in a development medium that promotes development and maturation of cotyledonary somatic embryos that may, for example, be placed on germination medium to produce germinants, and subsequently transferred to soil for further growth, or alternatively, placed within manufactured seeds and sown in soil where they germinate to yield seedlings. Manufactured seeds are described, for example, in U.S. Pat. Nos. 5,564,224; 5,687,504; 5,701,699; and 6,119,395.

The somatic embryogenesis process typically is laborious and inefficient. For example, a labor intensive step in the embryogenesis process is the selective harvesting from development medium of individual embryos suitable for germination.

Efforts have been made to automate the harvesting of cotyledonary embryos. At the end of the development phase, the embryos may be present in a number of stages of maturity and development, and are typically attached to or imbedded in embryogenic suspensor mass. Separation and singulation are processing steps that occur at the end of development and maturation in which plant embryos are physically separated from each other and the underlying embryogenic suspensor mass (ESM) before further processing such as, for example, insertion into manufactured seed, or placement onto germination or pre-germination medium for further treatment prior to insertion into manufactured seed.

The present invention is directed to an automated system and methods for separating and singulating plant embryos in a sterile environment and on a commercial scale.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention is directed to an automated system for separating and singulating plant embryos comprising: a separation module constructed and arranged to separate a plurality of plant embryos from attached embryogenic suspensor mass, and sort the plant embryos according to size; a singulation module constructed and arranged to singulate the separated and sorted plant embryos into individual, discrete embryos, and to deposit the singulated embryos onto a porous substrate; a drying module constructed and arranged to dry the porous substrate upon which the singulated plant embryos are disposed; and a robotic arm, said robotic arm operable to transport the plant embryos from module to module in a predetermined sequence, wherein the robotic arm is programmable such that the robotic arm is not limited to move from module to module in the predetermined sequence, and wherein the robotic arm may move among the modules in response to one or more signals, and perform functions associated with separating and singulating plant embryos in addition to transporting the plant embryos from module to module, thereby optimizing the transport of plant embryos through the system and maximizing the use of each module to separate and singulate plant embryos. The automated system for separating and singulating plant embryos may further comprise a storage module for storing the plant embryos before the plant embryos are transported to the separation module. The automated system for separating and singulating plant embryos may further comprise a docking module for receiving plant embryos from the drying module, and for storing the plant embryos in containers that provide an environment suitable for further maturation of the plant embryos.

In one aspect, the present invention is directed to automated methods of separating and singulating plant embryos.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5A illustrates a view axial to the rotation of the spray apparatus shown in FIG. 5 indicating the direction of rotation of the spray apparatus and spray emanating from the nozzles.

FIG. 10 illustrates a perspective view of a docking module in accordance with one embodiment of the system of the invention.

DETAILED DESCRIPTION

Figure 1:
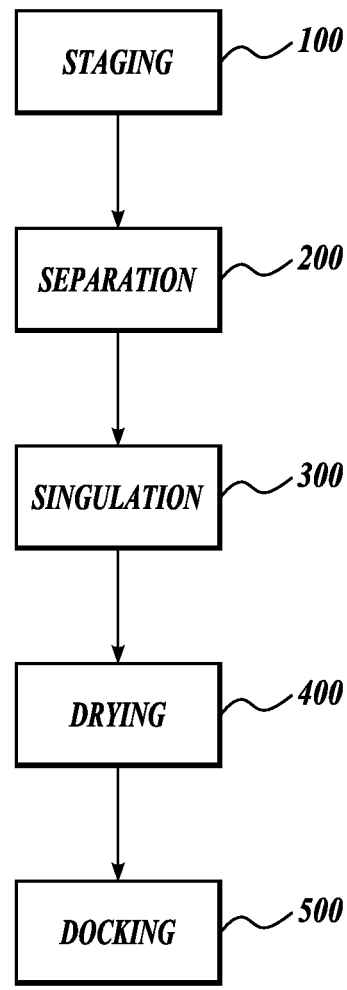
FIG. 1 is a flow diagram illustrating the process of separating and singulating plant embryos utilizing a representative embodiment of the system of the invention.

As used herein, the term "embryogenic suspensor mass" (ESM) refers to early stage embryos in the process of multiplication by budding and cleavage.

As used herein, the term "embryogenic tissue" refers to an aggregate of tens to hundreds of embryogenic cells that form an embryogenic suspensor mass.

As used herein, the term "plant embryo" refers to a somatic plant embryo. Somatic plant embryos may be produced by culturing embryogenic tissue by standard methods under laboratory conditions in which the cells comprising the tissue are separated from one another and urged to develop into minute complete embryos. As used herein, "plant embryo" includes embryos at various stages of development.

As used herein, the term "cotyledonary embryo" refers to an embryo that possesses one or more cotyledons. Cotyledonary embryos have a well defined elongated bipolar structure with latent meristem with cotyledonary primordia at one end and a potential radicle at the opposite end. The cotyledonary structure frequently appears as a small "crown" at one end of the embryo.

As used herein, the term "module" refers to a processing area or station.

As used herein, the terms "separate" "separation" refers to the process of separating cotyledonary embryos from attached embryogenic suspensor mass and sorting the embryos according to size.

As used herein, the terms "singulate" or "singulation" refers to the process of dispensing embryos on a substrate as individual, discrete embryos.

As used herein, the term "SAS" refers to the separation and singulation processes.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of: (1) initiation or induction, to initiate formation of embryogenic tissue, such as embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to multiply and mass produce embryogenic tissue; (3) development, to develop and form mature cotyledonary somatic embryos; and (4) post development steps such as separation, singulation, stratification, germination, growing into plants, such as through placement into manufactured seeds.

The somatic embryogenesis process is labor intensive. Efforts have been made to automate and scale-up the process to facilitate the production of tens of thousands of plant embryos. For example, the multiplication step may be carried out in a commercial-scale liquid bioreactor. At the end of the multiplication step, embryogenic tissue may be transferred to development medium for a period of time to develop into cotyledonary embryos. At the end of the development period, the cotyledonary embryos are to various degrees attached to and embedded in suspensor tissues and residual underdeveloped ESM, together with incompletely developed embryos, abnormally formed embryos, undersized or oversized embryos, and other pieces of non-embryo plant material, and to other embryos. It is important for subsequent normal germination to separate the embryos from the suspensor mass and from other embryos and to singulate the embryos into individual, discrete embryos.

Automating the separation and singulation steps is important for commercial scale-up of the embryogenesis process, as well as for productivity and worker well-being.

In one aspect, according to the present invention, an automated system for separating and singulating cotyledonary plant embryos is provided. A flow diagram of the process of separating and singulating plant embryos utilizing a representative embodiment of the system of the invention is illustrated in FIG. 1. Referring to FIG. 1, one embodiment of the separation and singulation system of the invention (referred to herein as the "SAS system") comprises five major stations or modules: (i) staging 100; (ii) separation 200; (iii) singulation 300; (iv) drying 400; and (v) docking 500. The embryos are transferred from module to module by use of a robotic arm. The modules and robotic arm are contained in a sterile enclosure. In one embodiment, the sterile enclosure is a HEPA-filtered laminar flow chamber.

A first module of the SAS system is referred to herein as the "staging module." The staging module 100 is used to store embryos developed en masse and attached to ESM until processing begins. In one embodiment, the developed embryos are stored on a porous membrane mounted in a frame, referred to herein as a development frame or "d-frame."

Figure 2:
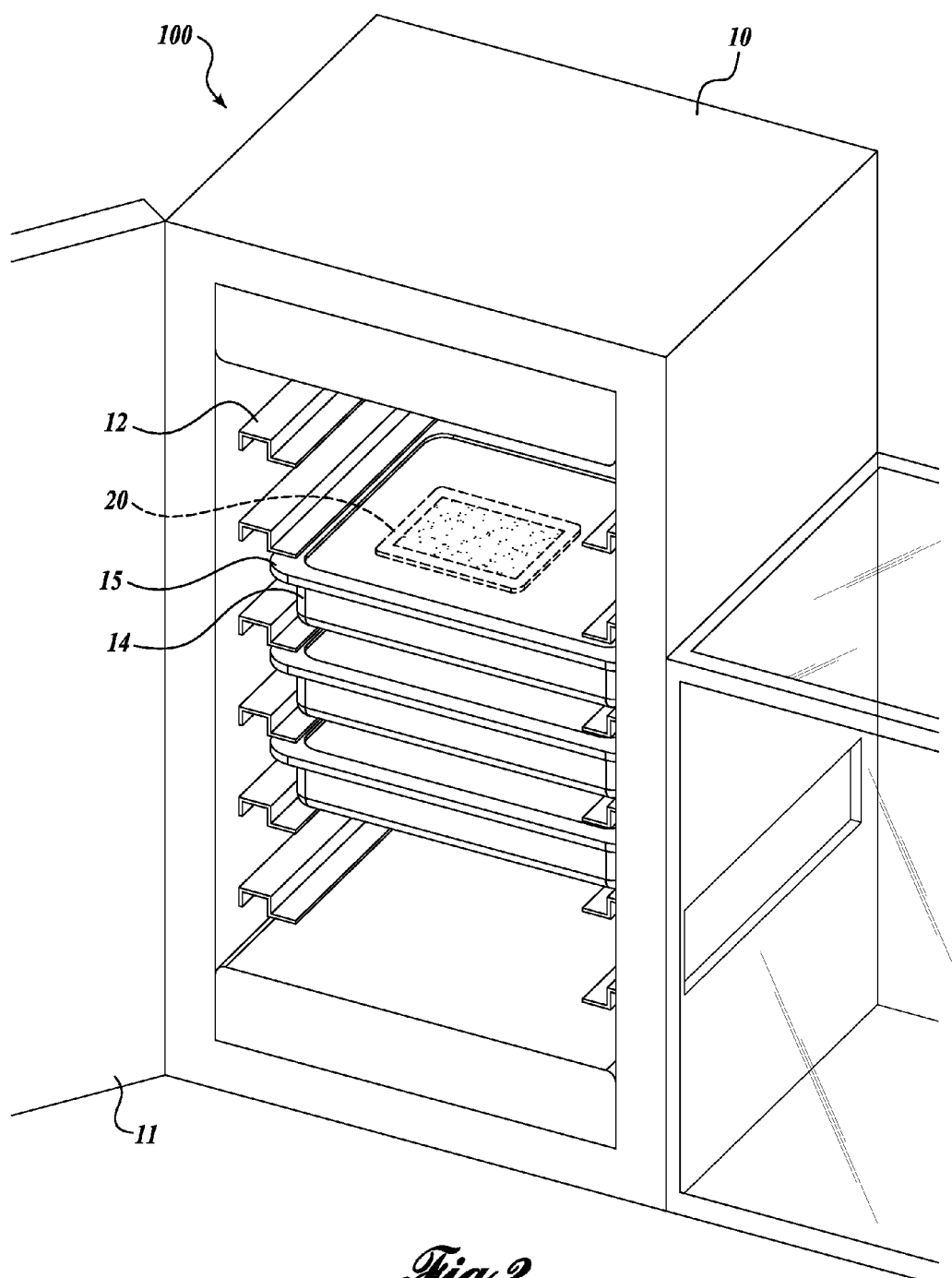
FIG. 2 illustrates a perspective view of a storage module in accordance with one embodiment of the system of the invention.

A representative embodiment of the staging module 100 is shown in FIG. 2. Referring to FIG. 2, the staging module 100 includes an insulated compartment 10 having a door 11 and one or more shelves 12 for storing one or more d-frames 20 containing disposed embryos. The d-frames 20 with disposed embryos may be transferred to the staging module from an area in which the embryos were developed and/or matured into cotyledonary embryos. The staging module 100 may store d-frames with or without development medium. The d-frames with disposed embryos may be stored in the insulated compartment 10 in containers 14 with lids 15. An elevator and slide system (not shown) may be used to transport a container 14 holding a d-frame 20 from the insulated compartment 10 to a presentation area 150 (Shown in FIG. 3) where the lid 15 is removed from the container 14 and the robotic arm picks up a d-frame 20 and moves it to the separation module 200.

Figure 3:
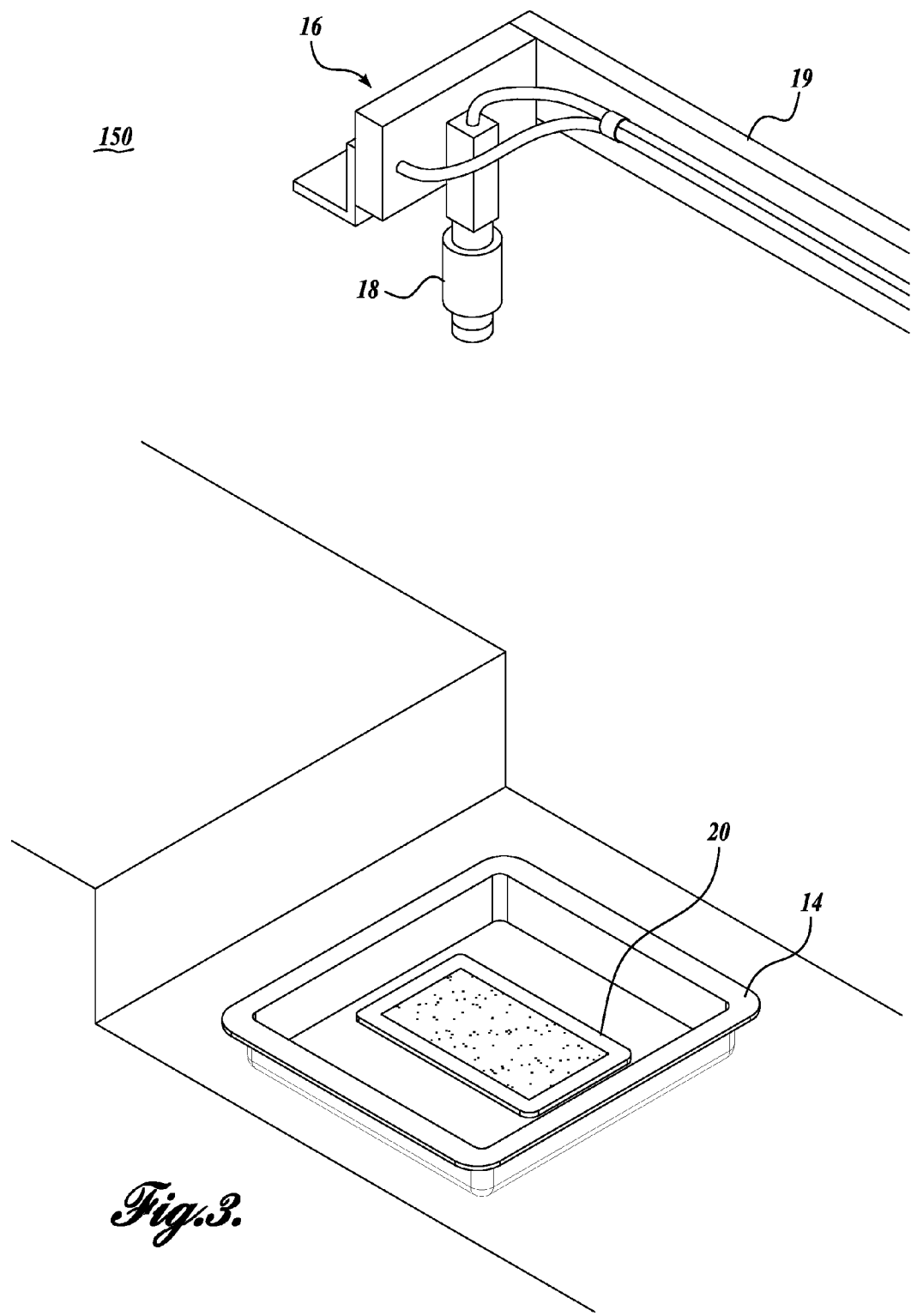
FIG. 3 illustrates a perspective view of a vision system in accordance with one embodiment of the system of the invention.

As shown in FIG. 3, in one embodiment, an overhead vision mechanism 16, having a camera 18 mounted in an arm 19, is used to locate the d-frame 20 inside the container 14 to assist the robotic arm in picking up the d-frame 20. Alternatively, the container 14 may be designed such that the d-frame 20 is precisely located within the container 14 and the robotic arm can pick up the d-frame 20 without the aid of a vision mechanism.

A second module of the SAS system is referred to herein as the "separation module." At the end of the development period, the cotyledonary embryos are to various degrees attached to and embedded in suspensor tissues and residual underdeveloped ESM, together with incompletely developed embryos, abnormally formed embryos, undersized or oversized embryos, and other pieces of non-embryo plant material, and to other embryos. It is important for subsequent normal germination to separate the embryos from the suspensor mass and from other embryos to yield individual embryos. The separation module 200 is used to separate developed embryos from the underlying suspensor mass and from each other, and to sort the embryos according to size.

Figure 4:
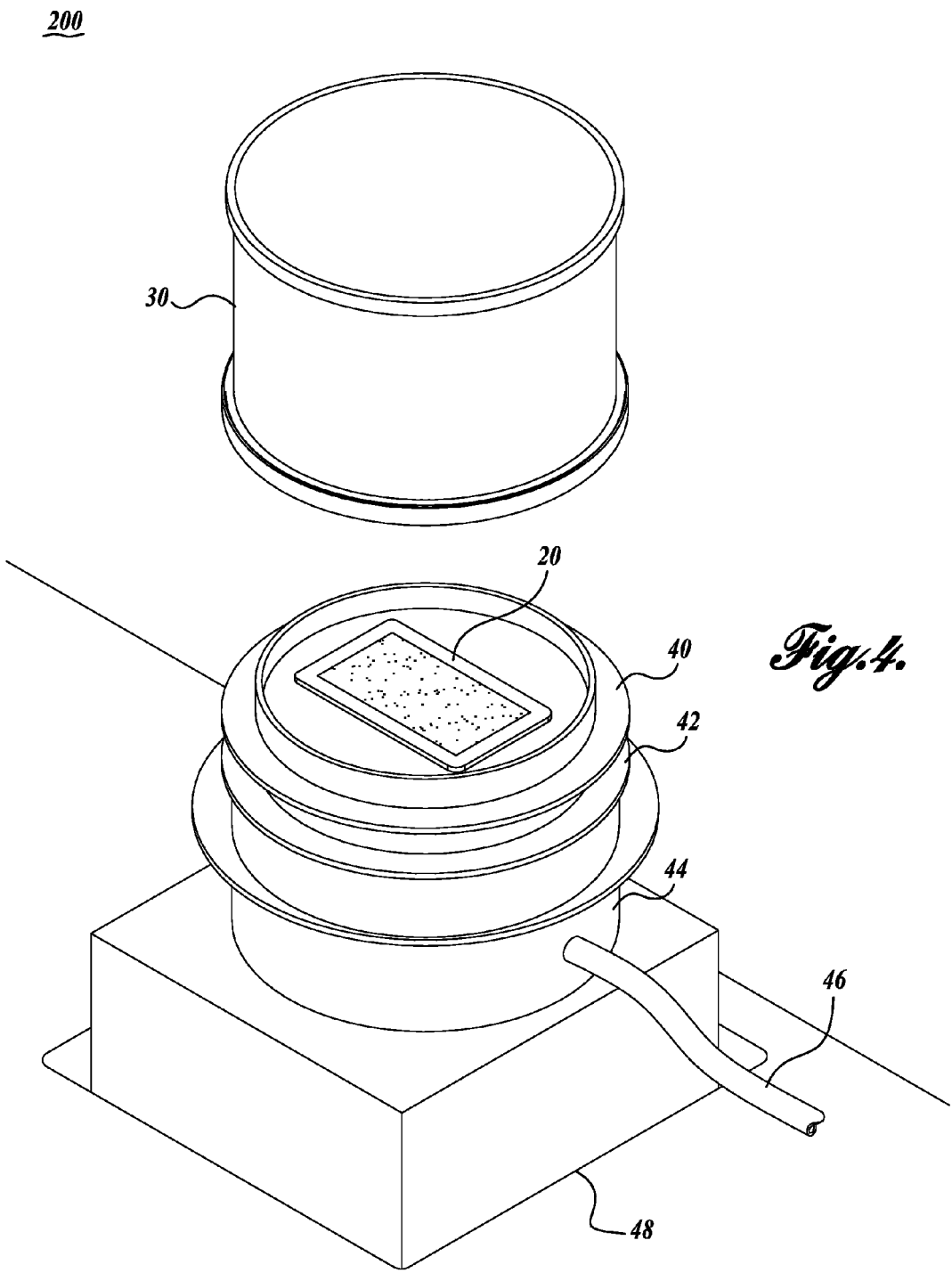
FIG. 4 illustrates a perspective view of a separation module in accordance with one embodiment of the system of the invention.
Figure 5:
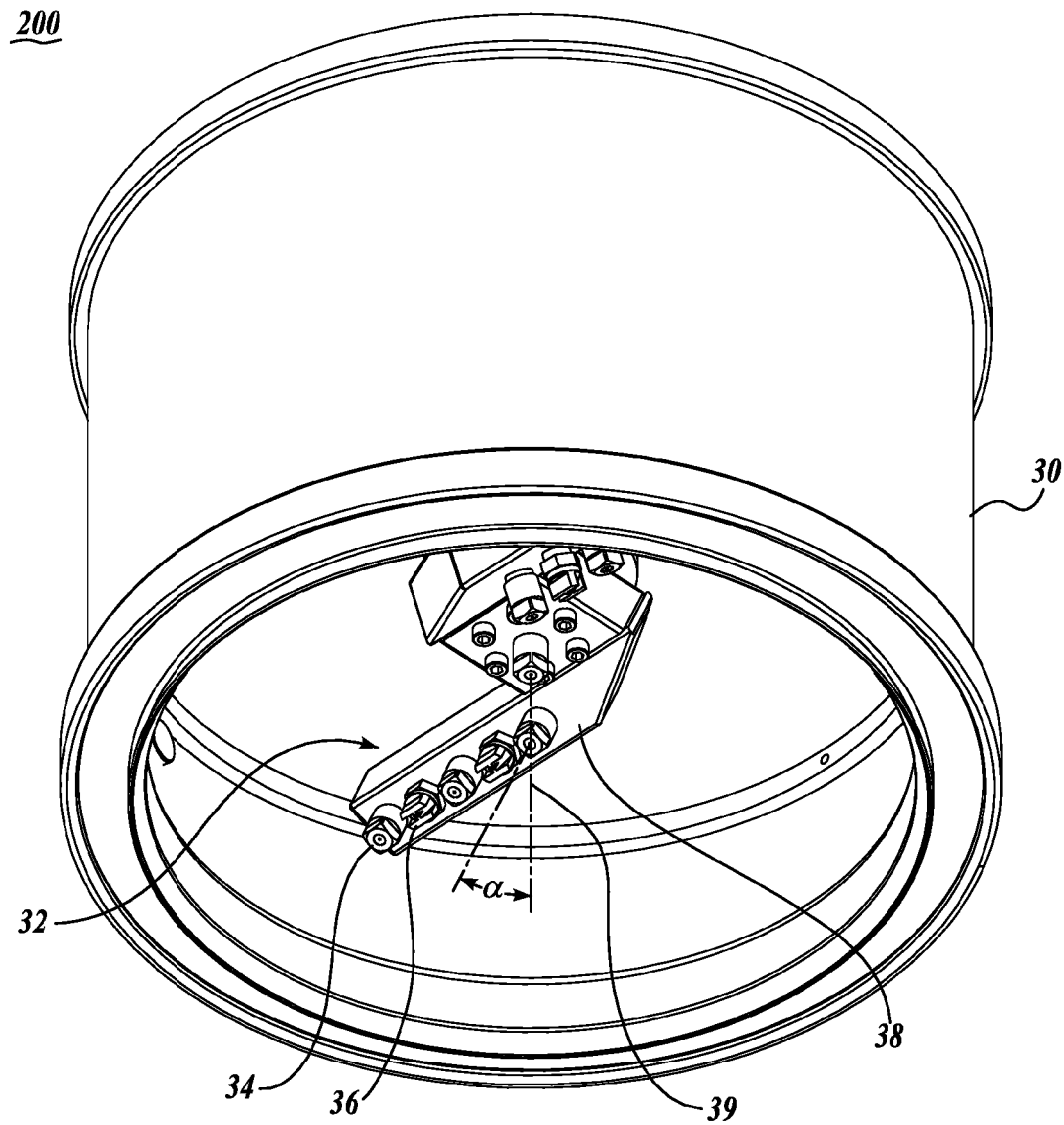
FIG. 5 illustrates a perspective view of a spray hood and spray apparatus in accordance with one embodiment of a separation module of the system of the invention.

A representative embodiment of the separation module 200 is shown in FIGS. 4 and 5. Referring to FIG. 4, the separation module 200 is shown as including a circular separation spray hood 30, one or more sieves 40 and 42, a separation vessel 44, and a lift mechanism 48. The separation vessel 44 is used to collect liquid and waste, such as embryogenic suspensor mass removed from the embryos, and embryos of undesired size or shape, resulting from the separation process, as further described below. The separation vessel 44 may be connected to an outlet 46 for removing the waste and liquid from the separation vessel 44. In one embodiment, the separation vessel 44 is disposed on top of the lift mechanism 48, and the one or more sieves 40 and 42 are in contact with, and stacked in a series on top of, the separation vessel 44. Referring to FIG. 5, a spray apparatus 32 is mounted to the underside of the separation spray hood 30. A spray apparatus suitable for use in the automated system of the invention is described in U.S. application Ser. No. incorporated herein by reference.

At the separation module 200, the robotic arm (not shown) inverts a d-frame 20, transferred from the staging module 100, places it on the top sieve 40, and thereafter the spray apparatus 32 sprays liquid on the inverted d-frame 20 to remove the disposed embryos and attached ESM from the d-frame 20.

More than one sieve may be used to separate the embryos from the ESM and to sort the embryos according to size. The mesh opening sizes of the sieve(s) 40 and 42 are selected so as to capture the desired sized embryos. The sieves 40 and 42 may be arranged in a stack such that a first sieve 40 with a first mesh opening size is placed on top of a second sieve 42 with a second mesh opening size that is smaller than the first mesh opening size. By way of example, the first sieve 40 may be of a mesh opening size such that embryos of the desired size, undersized embryos, and the embryonal suspensor mass pass through the first sieve 40, and embryos that are larger than the desired size are captured on the surface of the first sieve 40. The second sieve 42 may be of a mesh opening size such that embryos of the desired size are captured on the second sieve 42, and undersized embryos and the embryonal suspensor mass pass through the second sieve 42 into the separation vessel 44 and may be discarded through the outlet 46.

During the separation process, in one embodiment, the first sieve 40 is removed from the stack of sieves by the robotic arm and the oversized embryos are discarded. The second sieve 42 may be further sprayed by the spray apparatus 32 to facilitate the removal of undersized embryos and residual ESM. The second sieve 42, containing embryos of the desired size, is subsequently transferred by the robotic arm to the singulation module 300.

In some embodiments, more than two sieves may be used, each sieve having a different mesh opening size from the mesh opening size of each of the other sieves to further sort the embryos according to size/shape. For example, three sieves may be used, or even four sieves may be used. The mesh opening sizes may vary in the range from about 500 microns to about 2400 microns. For example, mesh opening sizes of 500, 850, 1000, 1180, 1400, 1700, 2000, and 2400 microns may be used. In one embodiment, the first sieve may have a mesh opening size of about 2400 microns. In one embodiment, the second sieve may have a mesh opening size of about 1400 microns.

By adjusting the mesh opening size/shape of the one or more sieves 40 and 42, only those embryos within a desirable size/shape range are selected, resulting in a population comprising mostly embryos separated from each other and substantially free of suspensor tissues.

Again referring to FIG. 5, a spray apparatus 32 is mounted to the underside of the separation spray hood 30. In one embodiment, the separation module utilizes a spray apparatus 32 comprising a plurality of spray nozzles that are configured to discharge spray patterns designed to push the plant embryos through the porous substrate and also move the embryos across the surface of the porous substrate. In one embodiment, the spray nozzles are selected from the group consisting of nozzles that discharge a cone shaped-spray pattern, a fan-shaped spray pattern, an oval-shaped spray pattern, and combinations thereof. In one embodiment, a combination of spray nozzles 34 and 36 are mounted on the rotatable arm 38 of the spray apparatus 32, wherein a first spray nozzle 34 discharges liquid in the form of a cone-shaped spray pattern; and a second spray nozzle 36 discharges liquid in the form of a fan-shaped spray pattern. In one embodiment, only nozzles 34 that discharge liquid in a cone-shaped pattern may be used. In one embodiment, only nozzles 36 that discharge liquid in a fan-shaped pattern may be used. Of course, other spray nozzles may be used, for example nozzles that discharge liquid in an oval-shaped spray pattern.

The spray nozzles 34 and 36 are shown as arranged on the spray apparatus arm 38 such that the spray nozzles 34 that discharge a cone-shaped spray pattern are alternated with the spray nozzles 36 that discharge a fan-shaped spray pattern.

The spray nozzles 34 and 36 perform different functions during the separation process. Spray nozzles 34, which discharge liquid in the form of a cone-shaped spray pattern, produce a gentle spray and cover a wide area. Spray nozzles 36, which discharge liquid in the form of a fan-shaped spray pattern, are particularly effective in removing the ESM from the embryos.

The spray apparatus is powered to rotate around a rotational axis 39. The spray nozzles are either configured or positioned along the spray arm 38 to cooperatively provide substantially uniform spray coverage during rotation of the spray arm 38. The spray nozzles 34 and 36 are canted relative to the rotational axis 39 of the spray apparatus. The spray nozzles 34 and 36 may be canted relative to the rotational axis 39 of the spray apparatus at an angle in the range from about 22° to about 25°, shown in FIG. 5 as "α".

As shown in FIG. 5A, the spray apparatus 32 rotates in a direction opposite to the direction that the spray nozzles 34 and 36 are canted such that the spray nozzles provide both a downward and tangential force on the plant embryos disposed on a sieve. The downward force pushes the embryos through the openings of the sieves 40 and 42. The tangential force moves the ESM and the embryos across the sieves 40 and 42. As the mesh of the sieve is uneven, the tangential force causes the plant embryos to wiggle on the sieve, and when they randomly orient in a vertical position, they present their slender profile to the mesh opening, thus allowing them to pass through the sieve if they are of the proper diameter. Without random wiggles, many of the embryos remain flat, and thus only expose their long axis to the mesh openings, and are less likely to pass through.

As shown in FIG. 5, the separation spray hood 30 surrounds the spray apparatus 32. During operation of the separation module 200, the lift mechanism 48 raises the separation vessel 44/sieves 40 and 42 assembly to engage the separation spray hood 30. The lift mechanism 48 can be of various constructions, including using linear actuators to effectuate the lifting of the sieves 40 and 42.

The spray hood 30 is of a shape and size such that it engages around the separation vessel 54 to form a seal, thus creating a closed spray system. The closed system contains the aerosols generated from the liquid spray emanating from the spray nozzles 34 and 36 of the spray apparatus 32, thereby reducing the spread of any contamination that may be present in the spray aerosols.

The separation spray hood 30 may further include a vent (not shown) through which air displaced by the spray emanating from the spray nozzles 34 and 36 is directed outside of the closed system.

Figure 6:
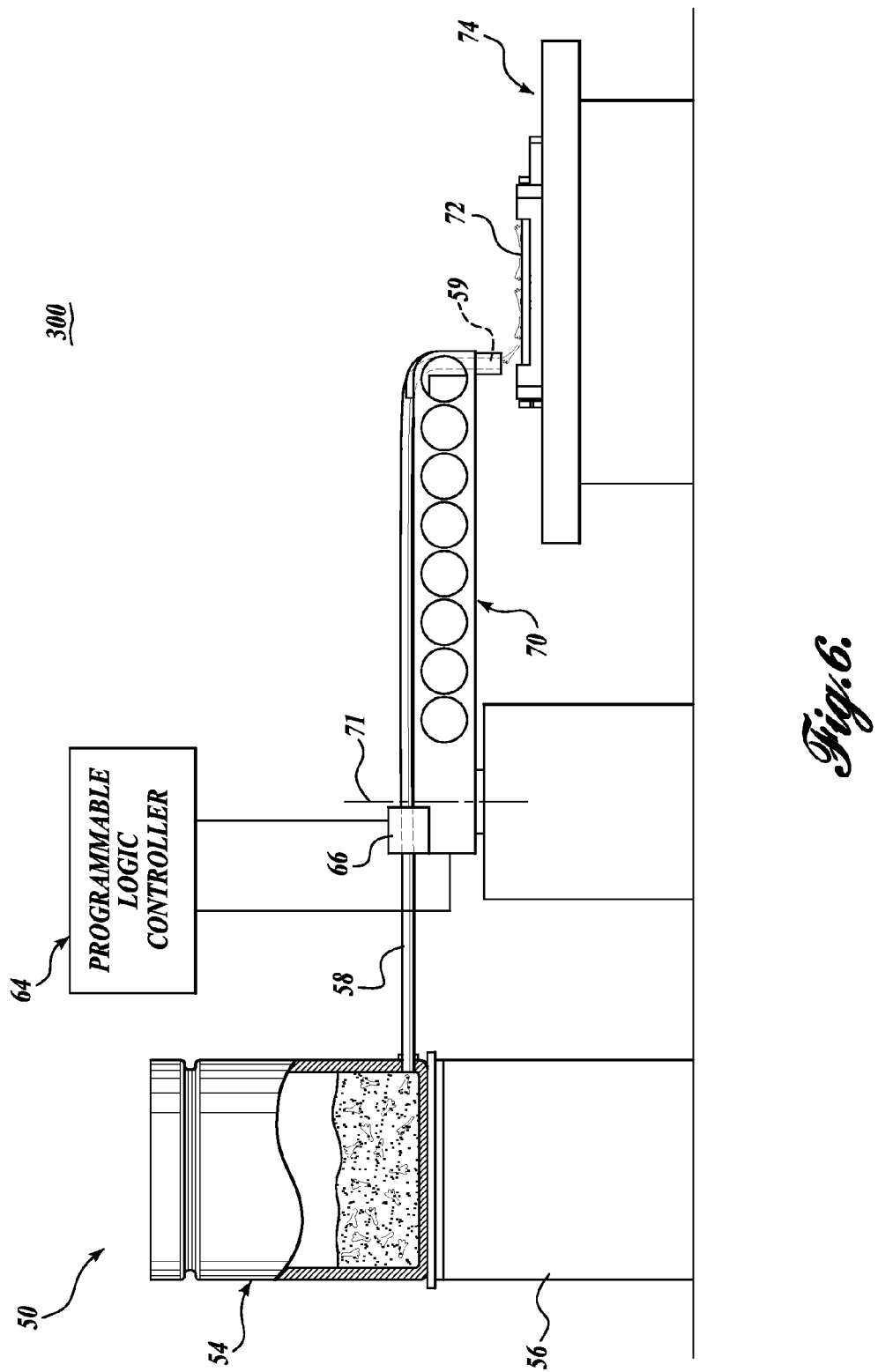
FIG. 6 illustrates a perspective view of a singulation module in accordance with one embodiment of the system of the invention.
Figure 7:
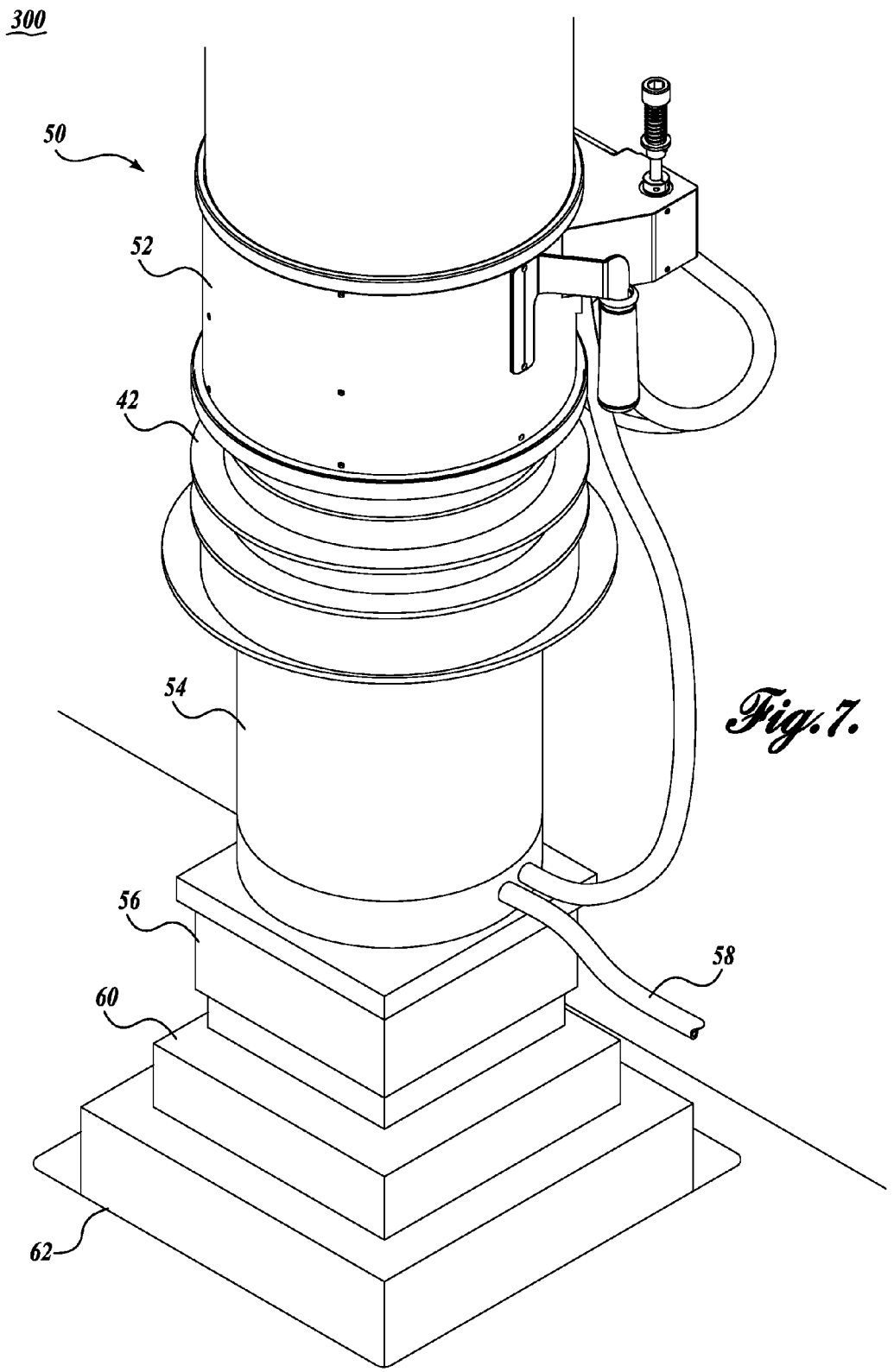
FIG. 7 illustrates a perspective view of an embryo dispensing assembly in accordance with one embodiment of a singulation module of the system of the invention.
Figure 8:
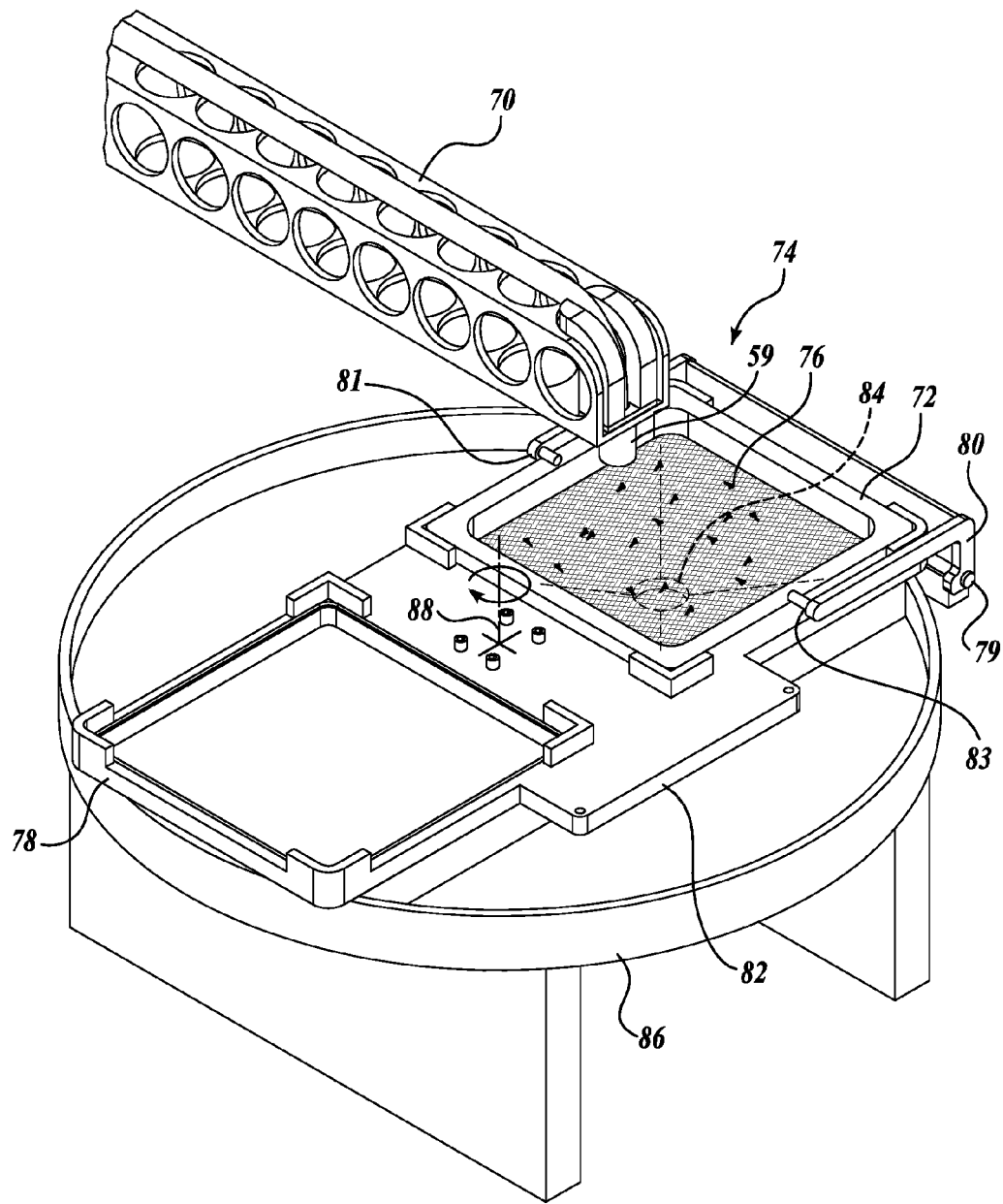
FIG. 8 illustrates a perspective view of an embryo deposit assembly in accordance with one embodiment of the singulation module of the system of the invention.

After processing at the separation module 200, the robotic arm may move the sieve 42 containing embryos of the desired size to a singulation module 300, which is the third module of the SAS system. The singulation module is shown in FIGS. 6-8. The singulation module 300 is used to deposit individual, discrete embryos onto a substrate in such a manner that the embryos are not touching each other or any object. Singulating the embryos into individual embryos allows the embryos to be subsequently imaged and robotically picked up for insertion into a manufactured seed.

During operation of the singulation module 300, embryos are deposited as individual discrete embryos onto a substrate. The substrate upon which singulated embryos are deposited may be a porous substrate mounted in a frame. A framed porous substrate suitable for use in the present invention is referred to herein as a singulation frame or "s-frame" 72. The porous substrate allows fluid to pass through while retaining embryos. The porous substrate may be of a color different than the color of the embryos so as to provide a contrast between the porous substrate and the embryo. One such porous substrate suitable for use in the singulation module 300 is Nitex® nylon, model No. 03-125/45 black color.

Describing the singulation module in more detail as shown in FIG. 6, in one embodiment, the singulation module 300 includes an embryo dispensing assembly 50, a programmable logic controller (PLC) 64, a singulation mechanism 70, which is used to deposit individual embryos on an s-frame 72, a sensor 66, an embryo dispensing tubing 58, and an embryo deposit assembly 74. Also, an s-frame 72 is shown in FIG. 6 disposed on the embryo deposit assembly 74.

Referring to FIG. 7, the embryo dispensing assembly 50 includes a singulation spray hood 52, to which is mounted a spray apparatus (not shown), a singulation vessel 54, a stir plate 56, a mass balance 60, a lift mechanism 62, and a sensor 66 (as shown in FIG. 6). An embryo dispensing tubing 58 extends from the singulation vessel 54. The singulation vessel 54 is in communication with the stir plate 56, which is disposed on the mass balance 60, which in turn is disposed on the lift mechanism 62, which is used to linearly raise or lower the singulation vessel 54. In one embodiment, the lift mechanism 62 may be an elevator, During operation, embryos are received at the embryo dispensing assembly 50 disposed on a sieve 42. The sieve 42 is inverted over, and placed on top of, the singulation vessel 54. Liquid emanating from the spray apparatus mounted to the singulation spray hood 52 is sprayed onto the inverted sieve 42 to dislodge the embryos from the inverted sieve 42 and into the singulation vessel 54. The spray apparatus is also used to supply the singulation vessel 54 with a suitable fluid, e.g. sterile water.

The lift mechanism 62 raises the singulation vessel/sieve assembly to engage the singulation spray hood 52. The spray hood 52 is of a shape and size such that it engages around the sieve 42 to form a seal, thus creating a closed spray system. The closed system contains the aerosols generated from the liquid spray emanating from the spray apparatus, thereby reducing the spread of any contamination that may be present in the spray aerosols.

The singulation vessel 54 is in communication with a stir plate 56 to stir the fluid in the singulation vessel 54 to a sufficient degree to maintain the embryos in suspension in the fluid. The stir plate 56 is in communication with the PLC 64 (shown in FIG. 6) to automatically adjust the amount of stirring that occurs. The PLC 64 is programmed so that the stirring speed linearly, or at another rate, decreases as the fluid level in the singulation vessel 54 decreases as embryos are dispensed from the singulation vessel 54 through the embryo dispensing tubing 58.

The embryo dispensing tube 58 extends between the singulation vessel 54 and the singulation mechanism 70. Embryos are transported from the singulation vessel 54 to the singulation mechanism 70 by fluid flowing through the embryo dispensing tubing 58. The flow rate of embryos through the tubing 58 is controlled by the lift mechanism 62, as further described below.

The fluid volume in the singulation vessel 54 is determined using a mass balance 60. The mass balance 60 is used to measure the mass of the fluid inside the singulation vessel 54. Mass is used to directly measure the flow rate of fluid exiting the singulation vessel 54, which is directly related to the time rate of mass decrease of the fluid in the singulation vessel 54; i.e., fluid exits the embryo dispensing tubing 58 at the outlet 59 of the singulation mechanism 70 at the same rate that mass decreases in the singulation vessel 54. Alternatively, mass may be used as an indirect measurement of "total head." As used herein, the term "total head" refers to the total hydrostatic pressure at the outlet 59 of the embryo dispensing tubing 58 (as shown in FIGS. 6 and 8) from the singulation mechanism 70, and it determines the flow rate of the fluid out of the singulation vessel 54.

The flow rate determines the velocity of the fluid in the embryo dispensing tubing 58. The velocity of the fluid in turn fixes the time of flight of the embryos through the embryo dispensing tubing 58, and thus controls when an embryo will exit the embryo dispensing tubing 58 at the outlet 59 of the singulation mechanism 70, and be deposited on the s-frame 72. The flight time is used to synchronize the motion of the singulation mechanism 70 with the exiting of the embryos from the singulation mechanism 70.

The flow rate of embryos flowing through the embryo dispensing tubing 58 is controlled by the lift mechanism 62. The lift mechanism 62 is used to raise or lower the singulation vessel 54, as required, to maintain the mass of fluid exiting the singulation vessel 54 per unit time fixed. Alternatively, when mass is used as an indirect measurement of total head, the lift mechanism 62 is used to raise or lower the singulation vessel 54, as required, to maintain a constant total head; i.e. a constant height between the outlet 59 of the embryo dispensing tubing 58 at the singulation mechanism 70 and the fluid level inside the singulation vessel 54.

The PLC 64 is in communication with the lift mechanism 62 to control raising and lowering of the lift mechanism 62.

The lift mechanism 62 raises the singulation vessel 54 at a fixed rate proportional to, or otherwise related to, the flow rate of fluid exiting the singulation vessel 54 to maintain a substantially constant flow rate. The singulation vessel 54 may be raised or lowered to increase or decrease, respectively, the flow rate.

In one embodiment, the embryo dispensing tubing 58 includes an inner diameter of a size to permit only a few embryos, for example one to three embryos, to enter the tubing 58 at any given time. Although only a few embryos enter the tubing 58 at a given time, multiple embryos may be positioned longitudinally within the tubing 58 over time. Depending on the size of the opening, the embryos may be positioned within the tubing 58 side by side, end to end, or a combination of positions. The number of embryos entering the tubing at any given time is generally controlled by creating increased turbulence at the outlet from the singulation vessel 54. This can be accomplished, for example, by placing a stir bar inside the singulation vessel 54 near the outlet from the singulation vessel 54, and by placing the stir bar in a well at the bottom of the singulation vessel 54 near the outlet. Additionally, controlling the density of embryos per unit volume of fluid in the singulation vessel 54 may assist in controlling the number of embryos entering the tubing at any given time. A suitable density for controlling the number of embryos entering the tubing at any given time may be, for example, around one embryo per 5 ml of fluid.

Minimizing the length of the embryo dispensing tubing 58 between the singulation vessel 54 and outlet 59 of the singulation mechanism 70, as well as minimizing obstructions in the flow path, are helpful to maintain a consistent and free flow of embryos through the embryo dispensing tubing 58.

In one embodiment, the embryo dispensing tubing 58 is composed of a material, such as silicone, that is transparent or semi-transparent to permit visual detection of an embryo within the tubing 58 by the sensor 66.

As shown in FIG. 6, a sensor 66 is suitably positioned on top of the singulation mechanism 70 just in front of the rotational axis 71 to sense and/or detect embryos within the tubing 58, and to detect when an embryo exits the singulation vessel 54. The sensor 66 is in communication with the PLC 64. The PLC 64 may be programmed to track the path of embryos within the tubing 58 and control the spacing and placement of embryos on the embryo deposit assembly 74.

The sensor 66 may be a laser-based visual sensor. One such sensor 66 is model No. LV-H300/100 Series, manufactured and sold by Keyence Corporation of Osaka, Japan.

The singulation mechanism 70 is used to deposit individual embryos on an s-frame 72. Again referring to FIG. 6, the singulation mechanism 70 is shown as being in the form of a robotic arm. The singulation mechanism 70 includes two drives to provide precise placement of embryos on an s-frame 72. A first drive causes movement of the singulation mechanism 70 in a first axis, for example, linearly back and forth in a direction along its length. A second drive causes movement of the singulation mechanism 70 in as second axis, for example rotating clockwise and counterclockwise. In one embodiment, the singulation mechanism rotates about vertical axis 71 over a very small angle, for example +/−11 degrees, depending on the size of the s-frame 72.

The axis of rotation 71 of the singulation mechanism 70 is located distal to the outlet 59 of the embryo dispensing tubing 58 such that the outlet of the embryo dispensing tubing 58 moves in an arc about axis 71.

In one embodiment, the singulation mechanism 70 is mounted on a rotary drive, which in turn is mounted on a linear drive. A suitable rotary drive is sold by Techno, Inc. of New Hyde Park, N.Y., part number HL36S0M26030. A suitable linear drive is sold by Parker Hannifin Corp. of Cleveland, Ohio, part number ER032BLTRA000D00FSRN0150A.

The combination of movement of the singulation mechanism in the first and second axes results in the deposit of the plant embryos onto the porous substrate in a two-dimensional array.

The singulation mechanism 70 is in communication with the PLC 64. The PLC 64 is programmable so as to permit an operator to adjust operational parameters. Operational parameters, such as the number of embryos placed on an s-frame 72, the spacing between the embryos, and the location of embryos on the s-frame 72 may all be programmed as desired.

The singulation mechanism 70 deposits embryos on an s-frame disposed on the embryo deposit assembly 74. Referring to FIG. 8, the embryo deposit assembly 74 includes a first singulation frame holding area 76 and a second singulation frame holding area 78, located side-by-side the first holding area 76, a retention mechanism 80, and a rotating mechanism 82. These components are mounted on an underlying frame structure 86.

The first singulation frame holding area 76 further comprises a vacuum source (not shown) that is in communication with an aperture 84 located in the center of holding area 76. During operation, the vacuum source is in communication with the s-frame 72 to rapidly remove fluid from the s-frame 72 and to aid in holding the deposited embryos in a fixed location on the s-frame 72.

The second singulation frame holding area 78 is used to hold an empty s-frame 72 awaiting transfer to the first singulation frame holding area 76, or alternatively, to hold an s-frame 72 with singulated embryos awaiting transfer to the drying module 400. The rotating mechanism 82 is used to support and to rotate s-frame(s) 72 about a central axis 88 between the first singulation frame holding area 76 and the second singulation frame holding area 78.

The retention mechanism 80 is pivotably attached to the first singulation frame holding area 76 via pivot rod 79, and is used to hold an s-frame 72 in place during singulation. To this end, the retention mechanism includes a pair of arms 81 that can be rotated about rod 79 to overlie the side margins of an s-frame 72. Pins 83 extend laterally from the distal end of arms 81 to bear against the side margins of the s-frame 72 at a location about midway along the length of the s-frame 72 side margins.

During transfer of s-frame(s) between the first singulation frame holding area 76 and the second singulation frame holding area 78, the retaining mechanism 80 pivots upward about rod 79 to relieve the s-frame 72, and the rotating mechanism 82 is raised and rotated 180 degrees about axis 88, thereby moving an empty s-frame 72 into the first singulation frame holding area 76, and moving an s-frame 72 with singulated embryos into the second singulation frame holding area 78. The rotating mechanism 82 is then lowered back into position, and the retaining mechanism 80 is returned to locking position over an empty s-frame 72.

During operation of the singulation module 300, an empty s-frame 72 is transferred from the second singulation frame holding area 78 to the first singulation holding area 76 by the rotating mechanism 82 and is positioned within the first singulation frame holding area 76 to receive singulated embryos from the singulation mechanism 70.

The SAS system of the invention may further include a wetting station (not shown) in which an empty s-frame 72 is immersed in water before being transferred to the second singulation frame holding area 78. Wetting the s-frame 72 is beneficial in aiding removal of fluid by the vacuum source 84 from the s-frame 72 during the singulation process.

The SAS system of the invention may include more than one singulation module 300, for example two singulation modules 300, to accommodate multiple sieves transferred from the separation module 200, thereby increasing efficiency and productivity.

After embryos are deposited on an s-frame 72 at the embryo deposit assembly 74, the s-frame 72 with disposed embryos may be transferred by the robotic arm to the fourth module of the SAS system, referred to herein as the "drying module." The drying module 400 is used to remove excess water from the substrate upon which the embryos are deposited at the singulation module 300, e.g., an s-frame 72. A variety of methods may be used to remove the water from the s-frames 72.

In one embodiment, the drying module 400 includes a mechanism to remove excess water by blowing dry air over and/or through the s-frames.

Figure 9A:
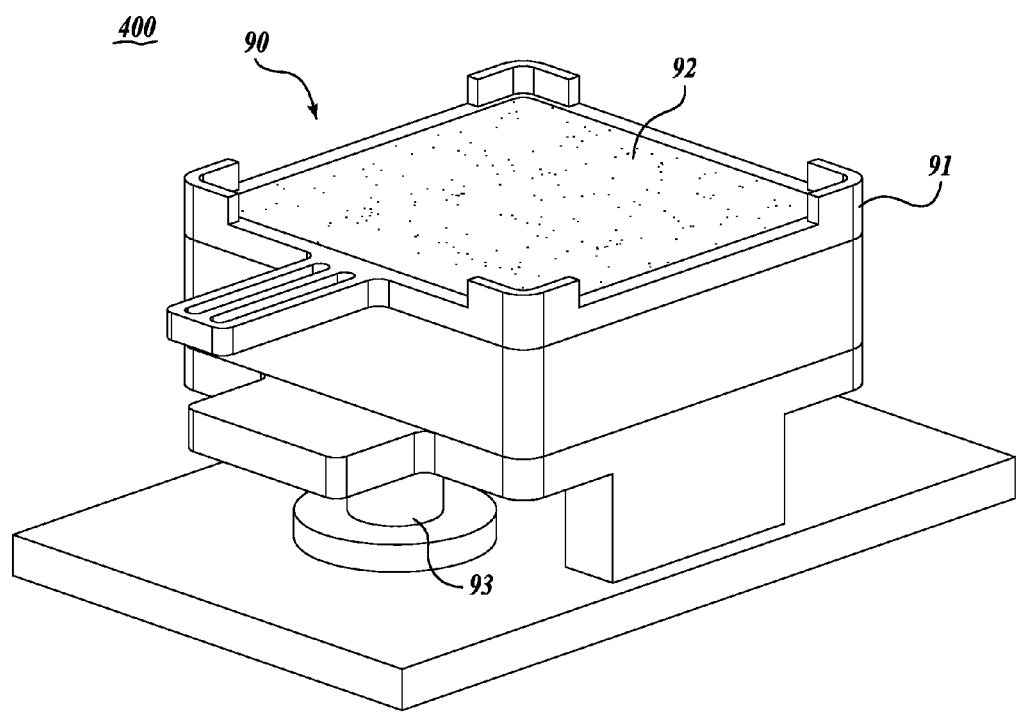
FIG. 9A illustrates a perspective view of a drying module in accordance with one embodiment of the system of the invention.

One embodiment of the drying module 400 includes a drying assembly 90, shown in FIG. 9A. The drying assembly 90 includes a porous substrate 92. The porous substrate 92 may be, for example, fritted glass or a porous metal sheet. The porous substrate 92 is disposed in a frame structure 91, which supports the porous substrate 92 over a vacuum source (not shown). During operation, an s-frame 72, with disposed embryos, is placed on the porous substrate 92. The porous substrate is brought into communication with a vacuum source through a pipe 93 and a vacuum is applied to remove water from the s-frame 72. The vacuum may be applied for a period of time for additional drying as the vacuum source moves air through the s-frame 72.

Figure 9B:
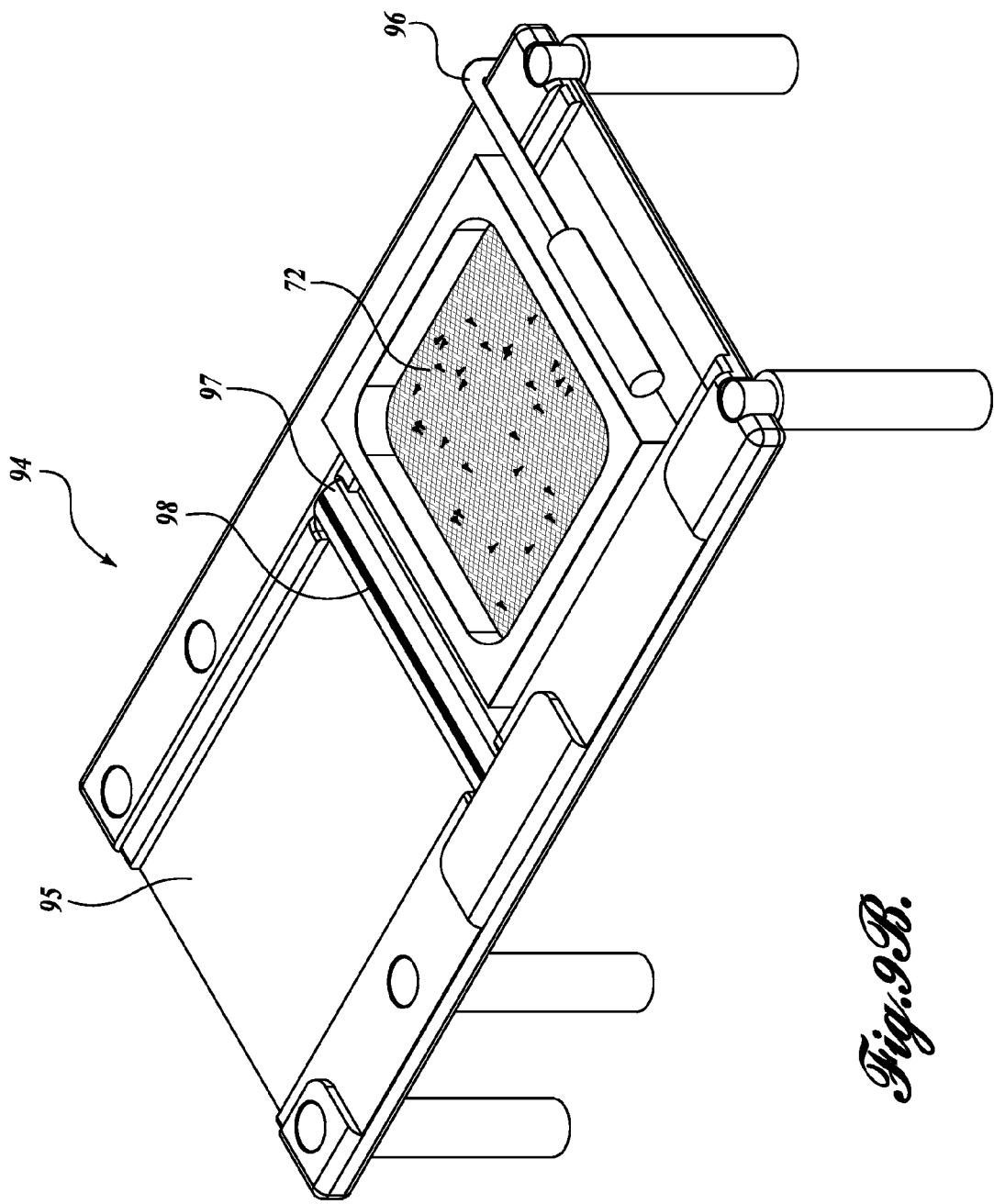
FIG. 9B illustrates a perspective view of a drying module in accordance with one embodiment of the system of the invention.

One embodiment of the drying module 400 includes a drying mechanism 94, shown in FIG. 9B. The drying mechanism 94 includes a platform 95 divided into two sections; a mechanical slide arm 96, driven by a motor (not shown); and a housing 97, which is located between the two sections of the platform 95, having a narrow elongated opening 98. The elongated opening 98 is in communication with a vacuum source (not shown).

During operation, an s-frame 72 with disposed embryos is placed onto a section of the platform 95. The mechanical slide arm 96 pushes the s-frame 72 across the opening 98 of the housing 97. As the s-frame 72 moves across the opening 98, the bottom surface of the s-frame 72 is in contact with the opening 98, which is in communication with the vacuum source, resulting in liquid being removed from the s-frame 72 and air being drawn over and around the embryos disposed on the top surface of the s-frame 72 and through the s-frame 72.

The SAS system of the invention may include more than one drying module 400, for example two drying modules 400, to accommodate multiple s-frames 72 transferred from the singulation module 300, thereby increasing efficiency and productivity.

After drying at the drying module 400, the s-frame 72 with disposed embryos may be transferred by the robotic arm to the fifth module of the SAS system, referred to herein as the "docking module" 500. As shown in FIG. 10, in one embodiment, the docking module 500 includes one or more containers 110, each having a door 112 and one or more shelves 113 for storing the s-frames 72 with disposed singulated embryos. In one embodiment the containers provide an environment suitable for further maturation of the plant embryos, for example conditioning over water. The docking module may be configured such that it can communicate with equipment used in processing the embryos after singulation and drying, for example inserting the embryos into manufactured seed or placing the embryos onto germination medium.

As described above, the SAS system of the invention comprises a number of modules or processing stations for separating and singulating embryos. During operation of the SAS system, embryos moves sequentially through the process from the staging module 100, to the separation module 200, to the singulation module 300, to the drying module 400, and finally to the docking module 500.

Figure 11:
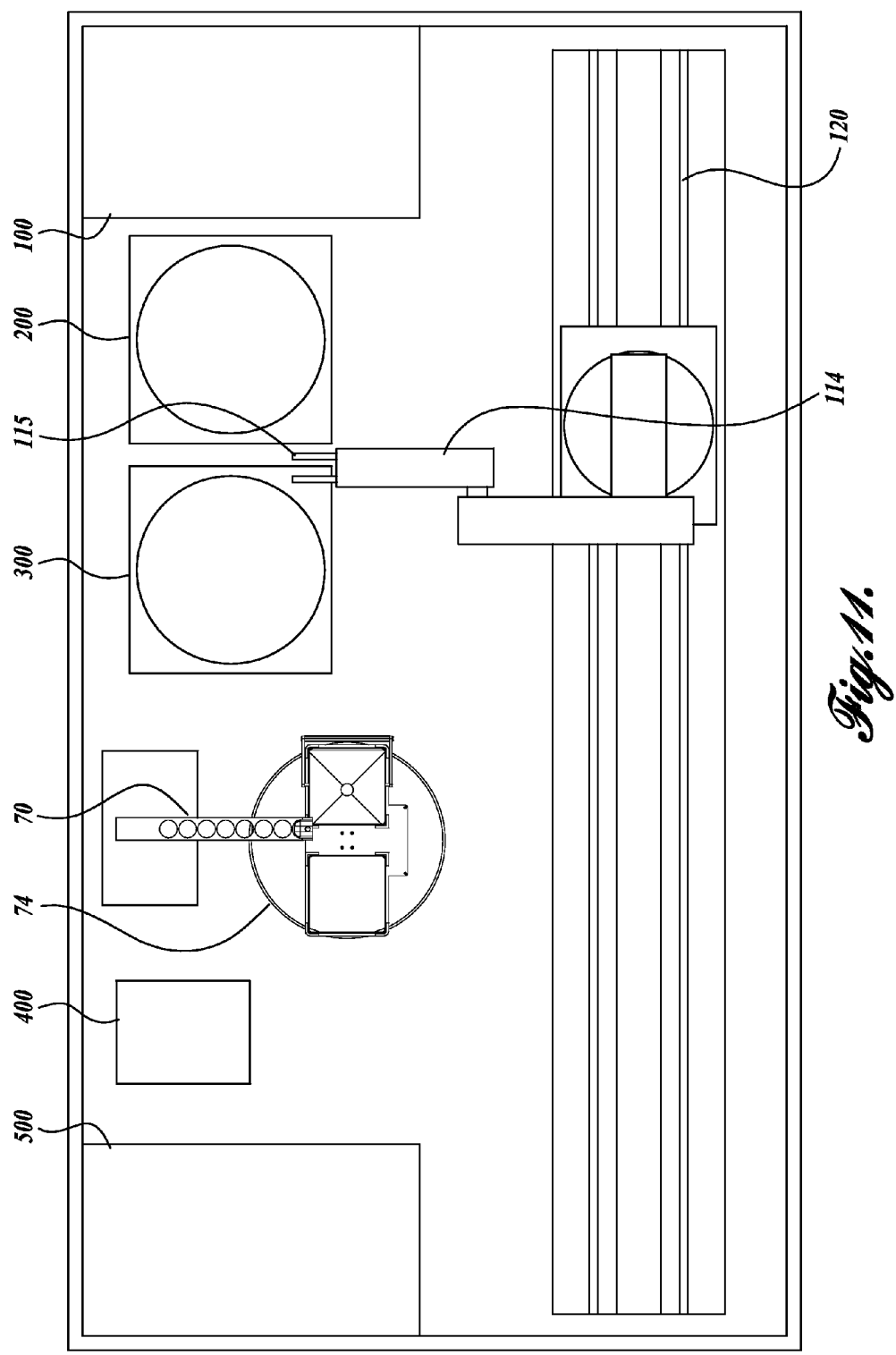
FIG. 11 illustrates a top planar view in accordance with one embodiment of the system of the invention.
Figure 12:
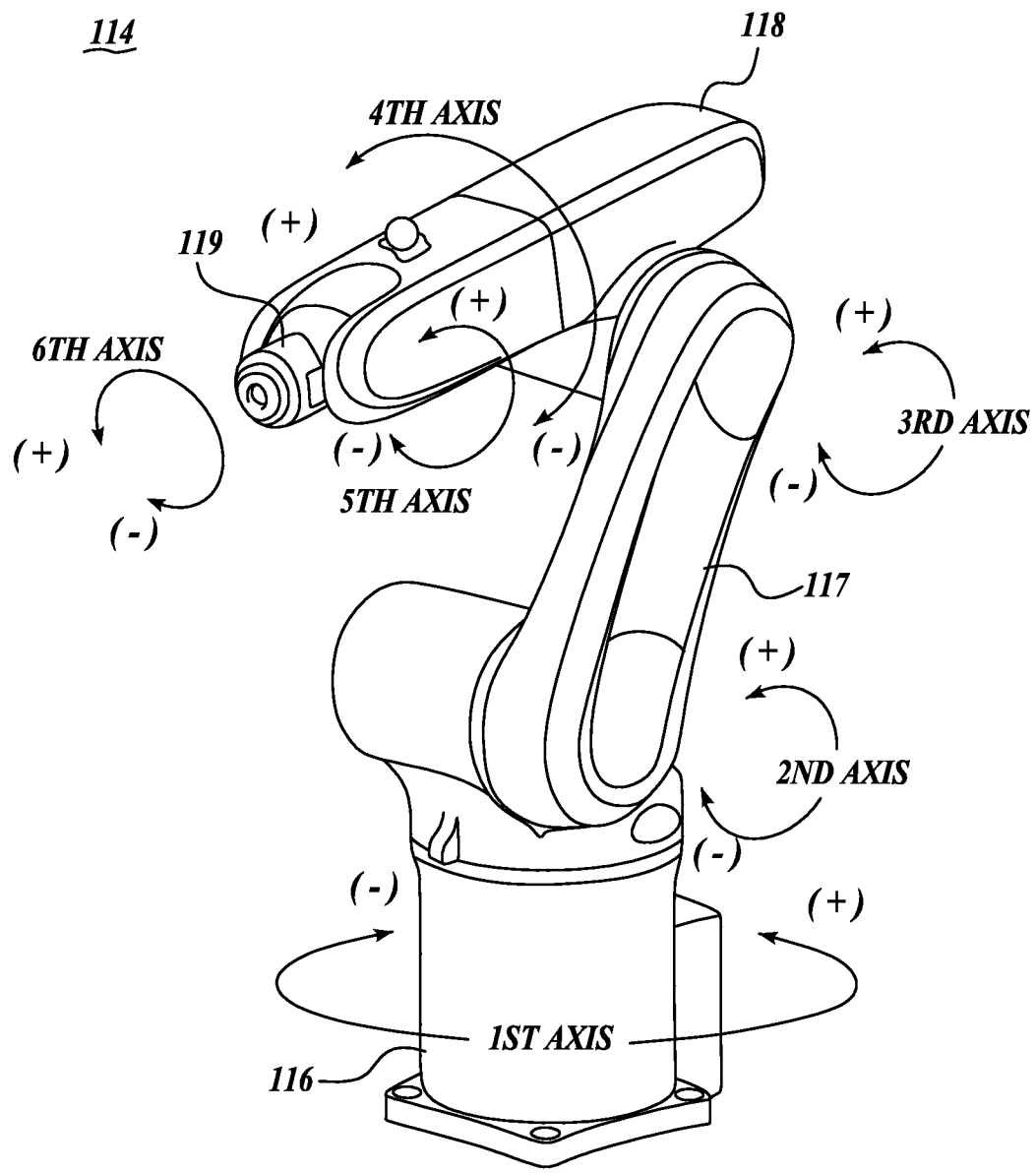
FIG. 12 illustrates a perspective view of a robotic arm in accordance with one embodiment of the system of the invention.

The embryos, disposed on porous substrates (e.g. d-frames 20, sieves 42, or s-frames 72) are transferred from module to module through the system by use of a programmable robotic arm 114 shown in FIG. 11. In one embodiment, the robotic arm 114 is in the form of a 6-axis articulating arm, as shown in FIG. 12, in communication with an external motion control device (not shown). Referring to FIG. 12, the robotic arm includes a base 116, a lower arm 117, an upper arm 118, and a wrist 119. The first axis, located at the base 116, allows the robot to rotate from left to right up to 180 degrees from the center point. The second axis allows the lower arm 117 to extend forward and backward. The third axis allows the upper arm 118 to raise and lower. The fourth axis rotates the upper arm 118 in a circular motion. The fifth axis allows the wrist 119 to tilt up and down. The sixth axis allows the wrist 119 to rotate in a circular motion. A suitable robotic arm and control device are sold by Denso Robotics of Long Beach, Calif., Model VS-6577G and RC7M, respectively.

The robotic arm 114 performs all material handling tasks between each processing station or module. For example, the robotic arm 114 may perform tasks such as, but not limited to, (i) picking-up a d-frame 20 from the storage module 100, transferring it to and from the separation module 200, and inverting it over the stack of sieves 40 and 42; (ii) picking-up a sieve 42 with disposed embryos and transferring it to the singulation module 300; (iii) picking-up an empty s-frame 72, transferring it to the wetting station, and then transferring it to the second singulation frame holding area 78; (iv) transferring an s-frame 72 with disposed embryos to the drying module 400; and (v) transferring an s-frame with disposed embryos from the drying module 400 to the docking module 500.

The robotic arm 114 performs other tasks, including, but not limited to, sieve stacking & parking as well as set-up and tear-down of components of the singulation module 300. The robotic arm 114 is not limited to performing tasks in a predetermined sequence. The robotic arm 114 performs task in variable sequences, as needed, thereby increasing efficiency and productivity. For example, the robotic arm can transfer a d-frame 20 to the separation module 200 and invert it over the sieve 40; pick up an s-frame 72 from the drying module 400 and transfer it to the docking module 500; then return to the separation module 200 to pick-up a sieve 42 and transfer it to the singulation module 300; etc.

Referring to FIG. 11, the robotic arm 114 is movably attached to a programmable linear slide structure 120 to provide the range of motion necessary to cover the large area encompassed by all the process modules and stations of the SAS system. In one embodiment, the slide 120 provides about 2.5 meters of travel along the length of the SAS system and is positioned by a seventh axis auxiliary control that is embedded into the robotic arm 114 external control device. The amount of travel may vary depending on the size of the SAS system. The linear slide 120 motion is fully integrated into the robotic arm 114 motion to precisely control the positioning of the robotic arm 114. The robotic arm 114 movements, as it performs the task associated with each module, and the motion of the robotic arm 114 along the liner slide 120, are controlled to minimize the robotic arm 114 passing over exposed embryos, thereby minimizing the probability of biological contamination transferring from the robotic arm 114 and its tools, described below, to the embryos.

In some embodiments, more than one robotic arm may be used. When multiple robotic arms are used, each robotic arm may be designated to perform one or more specific tasks. In some embodiments, the robotic arm(s) may be mounted to the ceiling.

In order to facilitate handling of d-frames 20, s-frames 72, and sieves 40 and 42 by the robotic arm 114, three specific end-of-arm tools are utilized. The tools are automatically exchanged by the robotic arm 114 as needed. The robotic arm 114 further comprises an automatic quick-change coupling device 115, shown in FIG. 11, to enable tool changes by the robotic arm 114. Each tool has a specific parking holder and location within the SAS system. The robotic arm 114 moves to the appropriate location to exchange tools, as needed. Each coupling device 115 further comprises multiple electrical circuits in communication with the robotic arm 114 controller to identify each tool with a unique circuit signal. After a tool change, the robotic arm 114 controller verifies that the robotic arm has picked up the intended tool.

The SAS system of the invention significantly increases productivity and rate of processing of embryos. In operation, the SAS system of the invention has achieved a production rate of about 100 singulated embryos deposited per s-frame, and about 35 s-frames processed per hour, which may result in about 3500 singulated embryos produced per hour, and about 28,000 singulated embryos produced in an eight hour period. By including more than one singulation module 300 and more than one drying module 400 in the SAS system, embryos can be processed through singulation and drying continuously, thereby greatly increasing the production rate.

Additionally, the components of the modules of the SAS system are designed to allow for rapid change-out for sterilization, and to change components, as needed, to process multiple clonal lines and avoid cross contamination between embryonic cell lines.

In one aspect, the present invention provides automated methods of separating and singulating plant embryos. The methods of the invention include the steps of: (a) depositing a plurality of plant embryos attached to embryogenic suspensor mass onto a first porous substrate; (b) spraying the plant embryos and embryogenic suspensor mass with a liquid discharged from a spray apparatus comprising a plurality of spray nozzles, wherein the spray nozzles are configured to discharge spray patterns designed to push the plant embryos through the porous substrate and also move the embryos across the surface of the porous substrate; and (c) transferring the plant embryos from step (b) to a singulation mechanism and depositing the embryos on a second porous substrate as individual, discrete embryos to produce singulated embryos.

In one embodiment, the first porous substrate is located on top of a stack of one or more porous substrates, each having a pore opening size. The porous substrates may be arranged in the stack according to pore opening size, in decreasing order, such that the substrate having the largest pore opening size is on top of the stack, and the substrate having the smallest pore opening size is on the bottom of the stack, thereby sorting the plant embryos according to size.

In one embodiment, the pore opening size of the porous substrates ranges from about 500 microns to about 2400 microns. Substrates of pore opening sizes of, for example, 500, 850, 1000, 1180, 1400, 1700, 2000, and 2400 microns may be used. In one embodiment, the porous substrate on the top of the stack may have a pore opening size of about 2400 microns, and the porous substrate on the bottom of the stack may have a pore size opening of about 1400 microns.

In one embodiment, the automated methods for separating and singulation plant embryos comprises the steps of: (a) transferring a plurality of plant embryos to a separation module constructed and arranged to separate a plurality of plant embryos from attached embryogenic suspensor mass, and sort the plant embryos according to size; (b) transferring the separated and singulated plant embryos from step (a) to a singulation module constructed and arranged to singulate the plant embryos into individual, discrete embryos, and to deposit the singulated embryos onto a porous substrate; (c) transferring the singulated embryos from step (b) to a drying module constructed and arranged to dry the porous substrate upon which the singulated plant embryos are disposed; and (d) wherein the plant embryos are transported from module to module by a robotic arm, said robotic arm operable to transport the plant embryos from module to module in a predetermined sequence, wherein the robotic arm is programmable such that the robotic arm is not limited to move from module to module in the predetermined sequence, and wherein the robotic arm may move among the modules in response to one or more signals, and perform functions associated with separating and singulating plant embryos, in addition to transporting the plant embryos from module to module, thereby optimizing the transport of plant embryos through the system and maximizing the use of each module to separate and singulate plant embryos.

The automated system and methods of the invention can be used to separate and singulate plant embryos from any plant species, such as dicotyledonous or monocotyledonous plants, gymnosperms, etc. Conifer embryos are suitable for use in the SAS system of the invention and may be from any conifer species including, but not limited to, species within the genera *Pinus*, *Picea*, *Tsuga*, *Pseudotsuga*, *Thuja*, *Juniperis*, *Larix*, and *Sequoia*.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An automated system for separating and singulating plant embryos comprising:
   a separation module constructed and arranged to separate a plurality of plant embryos from attached embryogenic suspensor mass, and sort the plant embryos according to size;
   a singulation module constructed and arranged to singulate the separated and sorted plant embryos into individual, discrete embryos, and to deposit the singulated embryos onto a porous substrate;
   a drying module constructed and arranged to dry the porous substrate upon which the singulated plant embryos are disposed; and
   a robotic arm, said robotic arm operable to transport the plant embryos from module to module in a predetermined sequence, wherein the robotic arm is programmable such that the robotic arm is not limited to move from module to module in the predetermined sequence, and wherein the robotic arm may move among the modules in response to one or more signals, and perform functions associated with separating and singulating plant embryos, in addition to transporting the plant embryos from module to module, thereby optimizing the transport of plant embryos through the system and maximizing the use of each module to separate and singulate plant embryos.

2. The automated system for separating and singulating plant embryos of claim 1, further comprising a staging module for storing the plant embryos before the plant embryos are transported to the separation module.

3. The automated system for separating and singulating plant embryos of claim 1, wherein the separation module further comprises:
   one or more sieves for receiving plant embryos and attached embryogenic suspensor mass, for separating the plant embryos from the embryogenic suspensor mass, and for sorting the plant embryos according to one or more desired sizes;
   a liquid spray source for forcing the embryogenic suspensor mass and plant embryos of undesired size through the sieves;
   a vessel for collecting liquid from the spray source, embryogenic suspensor mass, and plant embryos of undesired size.

4. The automated system for separating and singulating plant embryos of claim 3, wherein the liquid spray source comprises a spray apparatus, said spray apparatus comprising a plurality of spray nozzles, wherein the spray nozzles are configured to discharge spray patterns designed to push the plant embryos through the porous substrate and also move the embryos across the surface of the porous substrate, and wherein the spray nozzles are selected from the group consisting of nozzles that discharge a cone-shaped spray pattern, a fan-shaped spray pattern, an oval-shaped pattern, and combinations thereof.

5. The automated system for separating and singulating plant embryos of claim 1, wherein the singulation module further comprises:
   an embryo dispensing assembly for dispensing plant embryos in a fluid flow to a singulation mechanism;
   a singulation mechanism for receiving plant embryos from the embryo dispensing assembly, and for depositing the plant embryos onto a porous substrate in discrete embryos;
   an embryo deposit assembly for holding the porous substrate in place to receive plant embryos from the singulation mechanism; and
   a controller programmable to control the flow of plant embryos from the embryo dispensing assembly to the singulation mechanism, and to control the deposit of plant embryos by the singulation mechanism onto the porous substrate.

6. The automated system for separating and singulating plant embryos of claim 5, wherein the embryo dispensing assembly further comprises:
   a vessel for holding plant embryos suspended in a fluid;
   a mass balance for measuring the volume of the fluid in the vessel;
   a lift mechanism for raising and lowering the vessel to maintain a desired flow rate of fluid exiting the vessel; and
   a controller programmable to control the raising and lowering of the vessel by the lift mechanism, depending on the volume of the fluid in the vessel.

7. The automated system for separating and singulating plant embryos of claim 5, wherein the embryo deposit assembly further comprises:
   a first holding area for holding a porous substrate to receive plant embryos ejected from the singulation mechanism; and
   a second holding area for (a) holding a porous substrate until it can be transferred to the first holding area; or (b) holding a porous substrate with disposed embryos, which has been transferred from the first holding area to the second holding area.

8. The automated system for separating and singulating plant embryos of claim 7, further comprising a rotating mechanism for transferring a porous substrate between the first holding area and the second holding area.

9. The automated system for separating and singulating plant embryos of claim 7, wherein the first holding area further comprises a vacuum source in communication with the porous substrate to remove water from the porous substrate.

10. The automated system for separating and singulating plant embryos of claim 5, wherein the singulation mechanism further comprises:
    a first drive that causes movement of the singulation mechanism in a first axis; and
    a second drive that causes movement of the singulation mechanism in a second axis,
    wherein movement of the singulation mechanism in the first and second axes results in the deposit of the plant embryos onto the porous substrate in a two-dimensional array.

11. The automated system for separating and singulating plant embryos of claim 5, wherein the controller is programmable to control the number of plant embryos deposited on the porous substrate by the singulation mechanism, the spacing between the embryos on the porous substrate, and the location of embryos on the porous substrate.

12. The automated system for separating and singulating plant embryos of claim 1, wherein the drying module further comprises:
    a drying mechanism for removing liquid from the porous substrate upon which the plant embryos are disposed; and
    a vacuum source to facilitate the removing of liquid from the porous substrate by the drying mechanism.

13. The automated system for separating and singulating plant embryos of claim 1, further comprising a docking module for receiving plant embryos from the drying module, and for storing the plant embryos in containers that provide an environment suitable for further maturation of the plant embryos.

14. The automated system for separating and singulating plant embryos of claim 13, wherein the docking module is configured to communicate with equipment used in processing the plant embryos after singulation and drying.

15. The automated system for separating and singulating plant embryos of claim 1, further comprising one or more tools suitable to be coupled to the robotic arm through a coupling device, wherein each tool has a unique electrical signal, and wherein the coupling device further comprises multiple electrical circuits in communication with a controller of the robotic arm to identify the unique electrical signal of each tool.

16. The automated system for separating and singulating plant embryos of claim 1, further comprising a sterile enclosure for enclosing the modules of the automated system.

17. An automated method for separating and singulation plant embryos comprising the steps of:
    (a) transferring a plurality of plant embryos to a separation module constructed and arranged to separate a plurality of plant embryos from attached embryogenic suspensor mass, and sort the plant embryos according to size;

(b) transferring the separated and singulated plant embryos from step (a) to a singulation module constructed and arranged to singulate the plant embryos into individual, discrete embryos, and to deposit the singulated embryos onto a porous substrate;
(c) transferring the singulated embryos from step (b) to a drying module constructed and arranged to dry the porous substrate upon which the singulated plant embryos are disposed; and
(d) wherein the plant embryos are transported from module to module by a robotic arm, said robotic arm operable to transport the plant embryos from module to module in a predetermined sequence, wherein the robotic arm is programmable such that the robotic arm is not limited to move from module to module in the predetermined sequence, and wherein the robotic arm may move among the modules in response to one or more signals, and perform functions associated with separating and singulating plant embryos, in addition to transporting the plant embryos from module to module, thereby optimizing the transport of plant embryos through the system and maximizing the use of each module to separate and singulate plant embryos.

* * * * *